United States Patent [19]

Huang

[11] Patent Number: 4,839,111
[45] Date of Patent: Jun. 13, 1989

[54] PREPARATION OF SOLID CORE LIPOSOMES

[75] Inventor: Leaf Huang, Knoxville, Tenn.

[73] Assignee: The University of Tennessee Research Corporation, Knoxville, Tenn.

[21] Appl. No.: 9,427

[22] Filed: Feb. 2, 1987

[51] Int. Cl.$^4$ .................. A61K 9/66; A61K 37/22; B01J 13/02
[52] U.S. Cl. .................. 264/4.6; 264/4.3; 424/7.1; 424/450; 428/402.2; 436/829; 514/963
[58] Field of Search .................. 264/4.6; 428/402.2; 424/450; 514/963; 436/829

[56] References Cited

U.S. PATENT DOCUMENTS

| | | | |
|---|---|---|---|
| 4,235,871 | 11/1980 | Papahadjopoulos et al. | 264/4.6 X |
| 4,313,734 | 2/1982 | Leuvering | 436/525 |
| 4,425,334 | 1/1984 | Hunt | 424/101 X |
| 4,515,736 | 5/1985 | Deamer | 264/4.6 X |
| 4,618,685 | 10/1986 | McCully | 549/63 |
| 4,659,655 | 4/1987 | Rose | 436/824 X |
| 4,708,861 | 11/1987 | Popescu et al. | 428/402.2 X |
| 4,708,933 | 11/1987 | Huang et al. | 436/829 X |

FOREIGN PATENT DOCUMENTS 0216894 12/1984 Japan .................. 424/450

OTHER PUBLICATIONS

1986–1987 Aldrich Chemical Co. Catalog–Copyright 1986 by Aldrich Chemical Co., Milwaukee, WI., p. 599.

Primary Examiner—Richard D. Lovering
Attorney, Agent, or Firm—Ernest V. Linek; George W. Neuner

[57] ABSTRACT

Preferred solid core liposomes were prepared through four major steps:
(1) Preparation of prevesicles with encapsulated solid cores of agarose-gelatin by emulsification of agarose-gelatin sol in organic solvent containing emulsifiers followed by cooling;
(2) Extraction of lipophilic components from prevesicles to obtain microspherules of agarose-gelatin;
(3) In an optional step, colloidal gold particles were introduced into the microspherules, which were then coated with a protein or peptide molecule layer;
(4) Encapsulation of the microspherules was conducted using a modified organic solvent spherule evaporation method for the formation of the liposomes.

Electron micrographs indicate that if liposomes were prepared by using a lipid mixture containing dioleoyl phosphatidyl choline, cholesterol, dioleoylphosphatidylglycerol, and triolein (molar ratio 4.5:4.5:1:1), there was only a single continuous bilayer membrane for each solid core liposome.

12 Claims, 4 Drawing Sheets

Prevesicle with a solid core of agarose-gelatin network

Agarose-gelatin network (bare core)

Colloidal gold particles embedded in agarose-gelatin network

Solid core liposome encapsulated with colloidal gold particles

PREPARATION OF SOLID CORE LIPOSOMES

BACKGROUND OF THE INVENTION

Liposomes have been used as a delivery vehicle for sustained release of drugs, both in parental and topical applications (Weiner et al., *J. Pharmaceutical Sciences*, 74:922 (1985); Norley, et al., *J. Immunol.*, 1365:681 (1986)).

It is important that the rate of drug release from liposomes is slow with respect to the speed of the drug action. Ideally, zeroth-order release kinetics is needed for this purpose. In order to retard the drug release from liposomes, the present invention of "solid core liposomes," wherein a polymeric matrix, with or without embedded colloidal gold particles, is encapsulated in the interior aqueous compartment of a liposome, was developed.

Release of drugs, particularly proteins and polypeptides, from the "solid core liposomes" will be significantly retarded to achieve an improved sustained release kinetics.

SUMMARY OF THE INVENTION

The present invention is directed to a method for the encapsulation of solid cores in liposomes and to liposomes prepared by this method.

In general, the method of the present invention comprises the steps of:

(a) forming prevesicles with encapsulated solid cores consisting essentially of a polymer-gel sol in an organic solvent containing one or more emulsifiers;

(b) extracting lipophilic components from the prevesicles to obtain microspherules; and (c) encapsulating the microspherules in liposomes.

The present invention is also directed to a method for forming gold-labeled solid cores and the method for entrapping such solid cores in liposomes.

The use of these solid core liposomes, as drug delivery and diagnostic reagents, is also a part of the present invention.

DETAILED DESCRIPTION OF THE PREFERRED EMBODIMENTS

The solid core liposomes of the present invention can be prepared with or without colloidal gold labeling, and, in preferred embodiments, the gold-free liposomes can be employed in drug delivery systems, particularly for the topical or localized administration of liposome preparations as a sustained release drug carrier. See for example, Weiner et al., *J. Pharm. Sci.*, 74: 922-925 (1985) and Patel et al., "Liposomes: From Physical Structure to Therapeutic Applications," Knight C. G. ed., Elsevier/North Holland Biomedical Press, Amsterdam (1981).

It is anticipated that the solid core liposomes of the present invention will have superior qualities over typical liposomes as drug delivery vehicles. For example, the polymeric matrix of the solid core will retard the premature release of macromolecules such as enzymes, peptides, and other water soluble therapeutic agents.

It is also known that colloidal gold particles are very adsorptive for proteins and peptides. Thus the gold-labeled solid core liposomes (AuSCL) of the present invention will also be suitable for use as drug delivery agents, especially for the sustained release of macromolecules, therapeutic agents, and the like.

In addition, the solid core liposomes of the present invention have provided a new opportunity for the use of colloidal gold to label liposomes which can then either be examined under the light microscope or detected by electron microscopy. The gold labeled solid core liposomes may also be employed in immunoassays because of their ease of detection.

With the preparation method of the present invention, it is anticipated that future studies of liposome-cell interactions will be easier to conduct.

The internal solid core of the AuSCL may also increase the mechanical stability of the liposomes.

Figure 1:
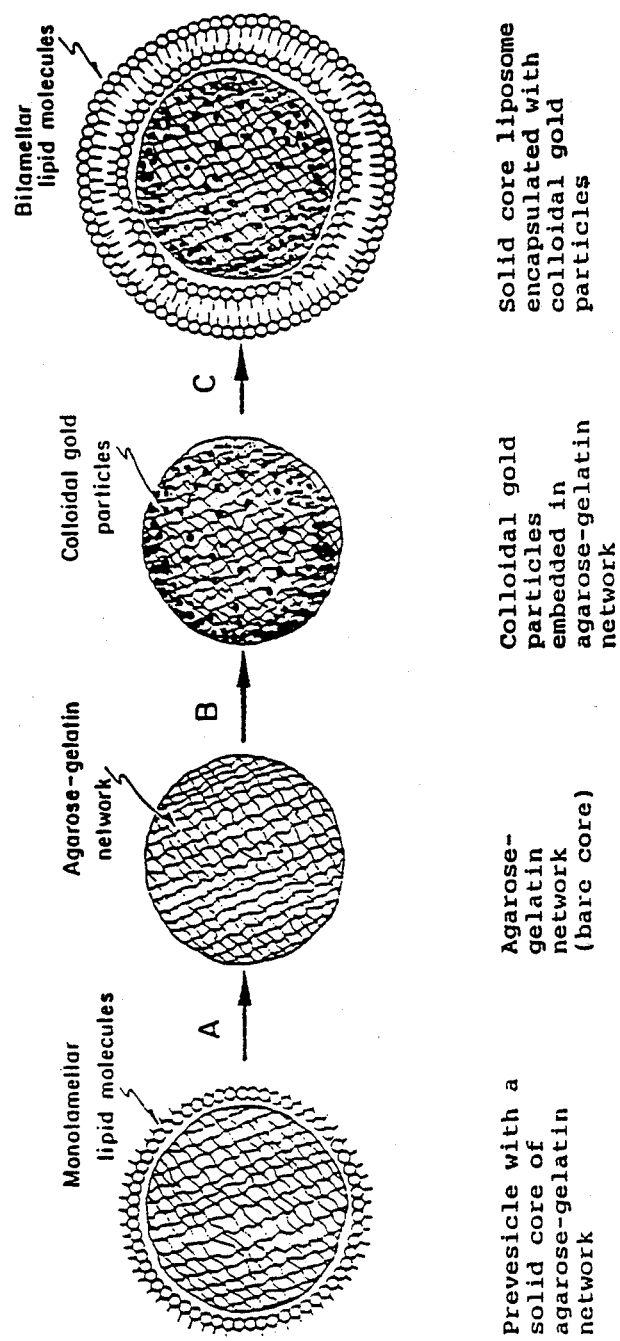
FIG. 1 is a schematic representation of the process steps of one preferred embodiment of the present invention.

As illustrated in FIG. 1, the procedure for preparing the AuSCL of the present invention requires two steps. First, the solid core portion is prepared, then this is incorporated into the liposomes.

The solid core should be prepared from a polymeric gel composition having an open matrix structure. The preferred solid core was made up from a suspension of agarose and gelatin.

Preferably, the solid core was prepared by the emulsification of a warm (about 70° C.) aqueous mixture of agarose and gelatin. Additional ingredients included n-octylglucoside, Hepes buffer, EGTA, NaCl, calcein and glass beads) with an organic phase containing cyclohexane, egg lecithin and Span 80 (as emulsifiers) and absolute ethanol as a co-surfactant).

In general, the emulsification procedures were performed at room temperature (i.e., "under warm conditions") and included both vortexing and sonication. The resulting emulsion was then cooled down (below about 10° C., preferably to about 4° C.) to obtain solidified microspherules of agarose-gelatin (i.e., "solid cores") dispersed in the organic solution.

In early experiments it was difficult to emulsify the agarose-gelatin mixture. However, when the preferred "mixed system" was employed, i.e., with surfactants in both the aqueous and the organic phases, an emulsion of agarose-gelatin dispersed in cyclohexane was readily obtained.

As set forth above, the mixture of reagents used to make the agarose-gelatin emulsion is relatively complex, but preferably, none of them (or their functional equivalents) should be omitted.

Lecithin and Span 80 are preferably the main emulsifiers for the organic phase although other known emulsifiers may also work. Ethanol works as a co-surfactant, and N-octylglucoside is preferred for the agarose-gelatin mixture, if the resulting product is to be finely dispersed.

The preferred molar ratio of N-octylglucoside to egg lecithin in this invention is about 1.5:1. If too much N-octylglucoside is added to the aqueous phase, the melted agarose-gelatin mixture does not gel when incubated at low temperatures (e.g., in an ice bath).

The preferred concentration of ethanol in the organic phase is adjusted to about 3%. If too much ethanol is added to the organic phase, it causes leakage of the prevesicles.

The crude emulsion is not homogeneous; it consists of agarose-gelatin microspherules of different sizes, generally ranging from less than about 0.5 microns to greater than about 6 microns.

These different sized microspherules can be fractionated by centrifugation, and are generally divided into three groups.

Small microspherules have an average diameter of about 0.5 microns. Medium-sized microspherules are about 0.5-2.5 microns, and large microspherules have a diameter greater than about 2 microns.

The small microspherules were much more homogeneous in size than any of the other microspherules obtained and were easily penetrated by tannic acid and gold chloride which were used in preparing the colloidal gold. The quality of these microspherules was superior to those of the other two groups, but the yield of preparation of this group was low (only about 1% of the total volume of the original agarose-gelatin used).

The medium-sized microspherules were most abundant. They were also readily labeled with colloidal gold particles. The only difference in preparing these microspherules from the larger microspherules was that these were collected at a relatively low centrifugation speed (about 3000 rpm).

In preferred embodiments of the present invention, centrifugation was employed as the means for the fractionation of the microspherules. However, more homogeneous particles can be obtained by using other fractionation methods, such as sucrose density gradient centrifugation or by filtration through defined pore size filters.

The lipophilic components were extracted with several washes of the solid cores in cyclohexane, then in ether and finally in water.

The next step in the preparation of the solid core is the optional step of labeling them with colloidal gold.

The initial efforts in labeling centered upon alternating incubations with tannic acid and gold chloride. Using this procedure, the loading of colloidal gold particles in the microspherules was accomplished. However, the procedure was not entirely satisfactory because of the size heterogeneity of the resulting gold particles.

Nevertheless, the microspherules prepared by this known method contained enough colloidal gold particles to be easily seen using a phase-contrast microscope. They appeared rose-red and were monodispersed.

Figure 2A:
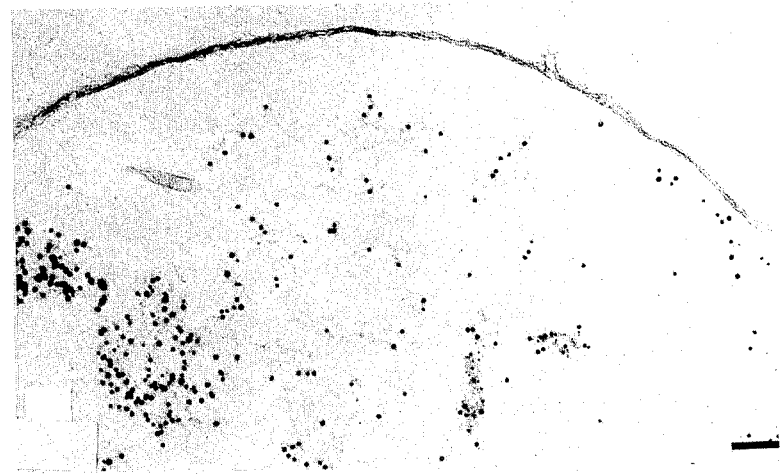
FIGS. 2 (*a, b & c*) represent thin section electron micrographs of AuSCL prepared according to the preferred procedure of the present invention (herein procedure "A"), showing a typical bilayer membrane of the liposome; (a) the bar = 0.1 microns; two whole AuSCL (b,c). There are some rod-like structures as well as some fibrous structures in the liposomes; the bar = 0.5 microns.
Figure 2B:
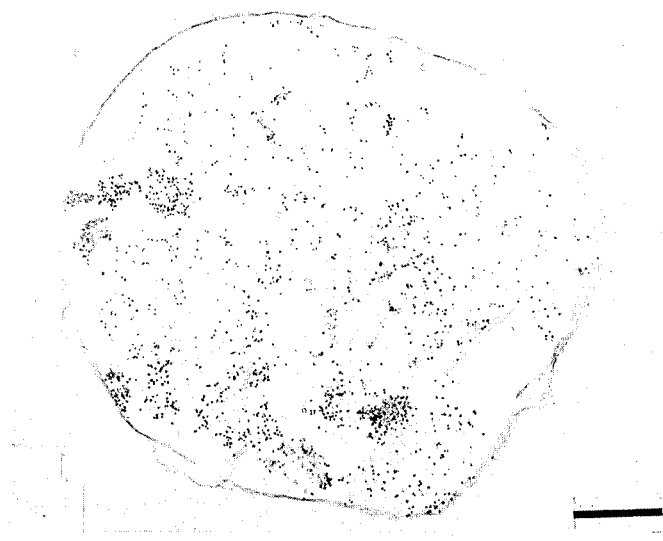
Figure 2C:
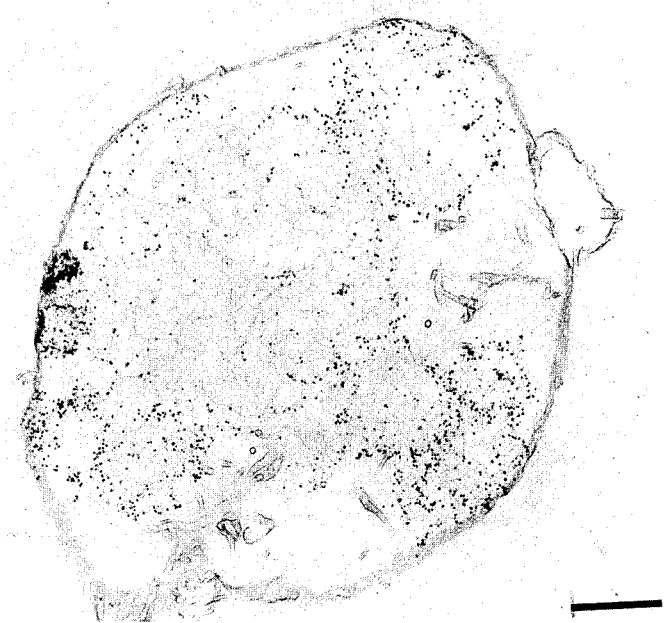

FIG. 2 is an electron micrograph or a thin section of medium-sized microspherules labeled with colloidal gold. The distribution of gold particles within microspherules was non-uniform. The peripheral areas of microspherules were heavily labeled with gold particles, whereas their central parts were not. This might have been caused by the slow tannic acid penetration, since tannic acid has a relatively large molecular weight and is mainly adsorbed by the gelatin located in the outer part of the microspherules.

As an alternate method, there was selected maleate buffer, pH 6.0, for coating of the colloidal gold particles with both BSA and IgG. It is known that adsorption of various proteins on the colloidal gold particles is significantly affected by the pH of the solution, which should be near the pI of the protein for maximum yield (Horisberger, supra).

In one preferred embodiment, colloidal gold particles were introduced into the solid cores by the following procedure; the solid cores were first dispersed in 100 fold (v/v) 0.05 M sodium hydrogen maleate buffer, pH 6.0, containing 0.06% tannic acid. About 15 min. later, an equal volume of 0.12% gold chloride was added while the mixture was sonicated in a bath type sonicator.

The reaction between tannic acid and gold chloride predominantly occurred within the solid cores with most of the colloidal gold particles formed in the outer zone of every solid core. The resulting agarose-gelatin solid cores containing colloidal gold particles (AuSC) were washed several times in water.

Liposomes with encapsulated agarose-gelatin solid core containing colloidal gold particles (AuSCL) were prepared by employing a modification of the organic solvent spherule evaporation method (OSSE) (see, Kim et al., *Biochim. Biophys. Acta*, 728: 339-348 (1983) and Kim et al., *Biochim. Biophys. Acta*, 812: 793-801 (1984)).

The lipid composition useful in the present invention most preferably includes triolein. Other preferred components include neutral phospholipids such as phosphatidyl choline and derivatives (e.g., dioleoyl) thereof; negatively charged lipids, especially phospholipids, such as phosphatidylglycerol and derivatives (e.g., dioleoyl) thereof; and cholesterol.

Depending upon the concentration of the lipids in the liposome formulation, the skilled artisan will be able to formulate either unilamellar or multilamellar liposome vesicles.

Two different procedures for preparation of AuSCL were compared as a part of the present invention:

Procedure A:

Pelleted AuSC (average diameter around 0.5 microns, but larger ones could also be used) were washed twice and resuspended by sonication in a solution of a protein or a peptide, such as bovine serum albumin and $NaN_3$ and then collected by centrifugation, preferably at about 8000 rpm for about 15 min.

The protein treated AuSC were next washed with water and sucrose and collected by centrifugation, preferably at about 8000 rpm for about 15 min. Then, sufficient sucrose was added to make a suspension by sonication. The preferred concentration of the AuSC in this sucrose solution was about 5%.

This suspension was next transferred to an organic phase containing DOPC:Ch:DOPG:TO (4.5, 4.5, 1, and 1 micromoles, respectively) in a 1:1 mixture of chloroform ether. This mixture readily formed a W/O emulsion by hand shaking. The emulsified aqueous particles in suspension were further reduced in size by strong vortexing for about 10 min.

The W/O emulsion was next divided into two portions, and each portion was transferred to another tube containing sucrose. The W/O emulsion was again emulsified to form a W/O/W multiple emulsion.

The final W/O/W emulsion collected from both tubes was combined into a flask and the organic solvent was evaporated. The resulting AuSCL formed after the organic solvent had completely evaporated.

Next, dextrose were added to the AuSCL suspension and the liposomes were collected by centrifugation. The resulting pellets were resuspended in dextrose.

Procedure B:

Protein (e.g., BSA) coated and pelleted AuSC were dispersed in chloroform containing dipalmitoyl phosphatidylcholine and cholesterol. These AuSC were then collected by centrifugation at 8000 rpm for 20 min. at 4° C., and resuspended in DOPC:Ch:DOPG (9,9, and 1 micromoles, respectively) in 3 ml of Freon 114:ether (1:1), at 4° C.

After sonication for 1 min., the suspension was added dropwise to aqueous sucrose and ¼ strength L buffer, pH 7.4 (L buffer: 10 mM Hepes, pH 7.4; 1 mM EGTA and 150 mM NaCl).

This mixture was vortexed for 1 min., and evaporated with a stream of nitrogen at 4° C. for 10 min. and then continued at room temperature until all organic solvent was removed. The resulting AuSCL were dialysed overnight at room temperature against 1 liter of L buffer, pH 7.4, to remove residual organic solvent.

Figure 3A:
FIGS. 3 (*a & b*) illustrate thin section electron micrographs of AuSCL prepared with a prior art procedure (herein procedure "B"). It is evident that both multilamellar liposomes with multi-AuSC (a) and AuSC covered only by one lipid bilayer as part of a multilamellar liposome (b) as well an encapsulated AuSC (a and b) are seen in the preparation; The bar = 0.5 microns.
Figure 3B:
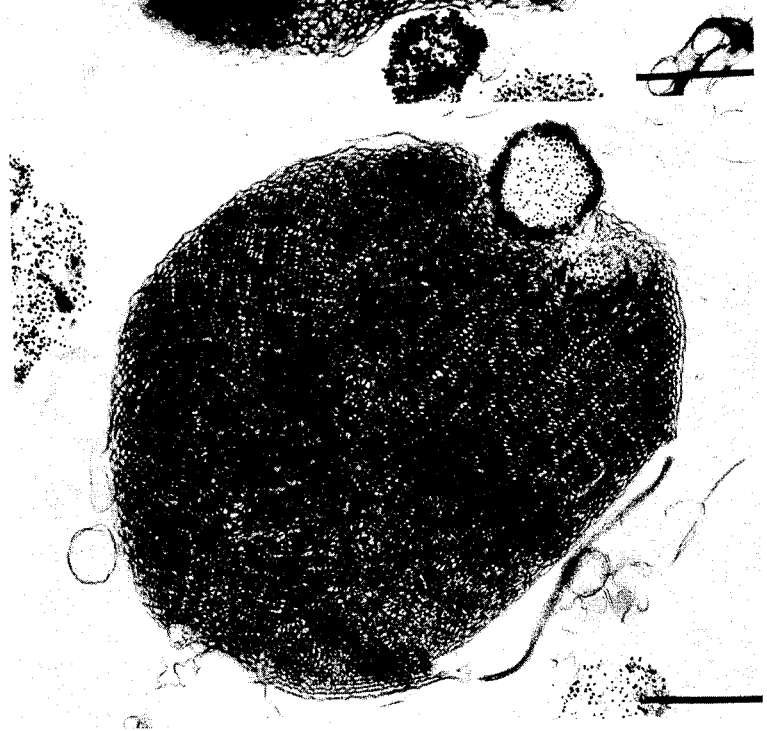

For the thin-section electron micrograph of FIG. 3, AuSCL obtained from procedure B were fixed in glutaraldehyde in phosphate buffer, pH 7.4, containing sucrose for 1 hr.; collected by centrifugation at about 500 rpm for 5 min.; post fixed in $OsO_4$ in phosphate buffer, pH 7.4, for 30 min.; washed with water overnight; pre-embedded in agarose and en bloc stained in uranyl acetate overnight; dehydrated through graded series of dioxane and embedded in LX-112 resin.

AuSCL obtained from procedure A (see, FIG. 2) basically went through the same procedures except for being post fixed in $OsO_4$ in L buffer, pH 7.4, and dehydrated with acetone. Ultrathin sections were cut with a diamond knife on a Reichert Om U3 ultramicrotome (Vienna) and collected on Formvar-coated copper grids. Samples were examined in a Hitachi H-600 electron microscope.

Since Au is electron dense, both AuSC and AuSCL can be seen under the electron microscope. The major difference between the liposomes produced by procedures A and B seems to be that when no TO was added to the lipid mixture, the liposomes had multilamellar and multivesicule structures and some of the AuSC were not enclosed by lipid membranes.

AuSC prepared with procedure A had a typical appearance of a bileaflet lipid membrane. The membrane looks very smooth and somewhat similar to the membrane of the red blood cell. Although there is only one bilayer membrane in every AuSCL, these membranes were continuous with no apparent holes.

Colloidal gold particles were abundant in every AuSCL. Some fibrous material (probably the poorly stained agarose-gelatin network) as well as some rod-shaped membraneous structures could be seen in the interior of some AuSCL.

It was apparent that multiple solid cores were entrapped in each AuSCL. The number of the solid cores per liposome depended on the diameter of the liposome. For example, about 5–6 cores were found in liposomes of 2–3 microns in diameter; about 10–20 cores were found in liposomes of approximately 5 microns in diameter.

From the results obtained, it was determined that the method of "Procedure A" was superior to the method of "Procedure B," because the AuSCL prepared with Procedure A were generally unilamellar with a relatively large volume of internal aqueous space. Furthermore, trapping the solid cores in liposomes with Procedure A seems to be a random event.

The preferred multiple emulsion system of the present invention consists of a water-in-oil-in-water (W/O/W) system, which is known to be rather unstable. (See, Matsumoto et al., *J. Coll. Interf. Sci.*, 52(2): 353–361 (1976) and Matsumoto et al., *J. Coll. Interf. Sci.*, 94(2): 362–368 (1982)). Thus, the lipid composition used for producing the preferred W/O/W system should have a suitable hydrophilic and lipophilic balance (HLB). (Florence et al., "Macro and Microemulsions" Shah, D.O. ed., Chpt. 23, pp. 360–380, American Chemical Society, Washington, D.C.)

In the preferred embodiments herein, dioleoyl phosphatidylglycerol (DOPG) seemed to flexibly form both concave and convex curvatures in the preferred multiple emulsion system. Thus, DOPG is suitable for W/O/W system formation. Since this is a negatively charged lipid, it may also prevent aggregation of individual W/O vesicles. From this data, it is believed that other negatively, charged lipids, especially negatively charged phospholipids, will also be useful in the present multiple emulsion system.

The role triolein (TO) plays may be similar to that of DOPG, i.e., it apparently makes the membrane more flexible and more fluid such that the lipid molecules may be favorably arranged into both concave and convex curvatures. However, other lipids with a suitable HLB could also suffice.

As described hereinabove, the solid core liposomes of the present invention (with or without gold labeling) may be used as sustained release drug delivery agents, both topically and parenterally.

Any accessible area of the body represents a potential site for the topical application of the sustained release liposomes of the present invention. The oral cavity, nasal passages, and upper respiratory tract, as well as the entire area of the skin and the genitalia are all sites of use for the present invention.

As used herein, the term "sustained release" refers to the slow release over time of the encapsulated drug from the liposomes at the site of application. Such sustained release provides a greater effective concentration of the drug at the site of application than does a single high dose of free (i.e., non-encapsulated) drug, because of the natural washing effect of bodily secretions which reduces the effectiveness of topically applied drugs.

The sustained release liposomes of the present invention may be used to entrap a variety of water soluble drugs from the antiviral, antimicrobial and antibiotic classes, just to name a few.

For topical applications, the sustained release, drug containing liposomes of the present invention may be administered directly to the site of application as a sterile aqueous suspension. Concentrations of the encapsulated drugs will of course be higher than those normally employed when free drugs are topically administered. The physician will be able to readily determine an appropriate dose.

For parenteral applications, the sustained release, drug containing liposomes of the present invention may also be administered as a sterile aqueous suspension. Concentrations of the encapsulated drugs will of course be higher than those normally employed when the free drug is parenterally administered. Again, the physician will be able to readily determine an appropriate dose.

The present invention thus represents a system for the delivery of therapeutic agents such that an effective therapeutic concentration is maintained at the site of application over an extended period of time, in comparison to the use of the same drugs in a non-encapsulated carrier.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

ABBREVIATIONS

As employed in the following examples (and elsewhere in the present specification) the following abbreviations are defined as follows:
- Au: colloidal gold particles
- AuSC: colloidal gold-labeled solid core(s) of agarose-gelatin
- AuSCL: solid core liposome(s) with encapsulated colloidal gold
- BSA: Bovine Serum Albumin
- Ch: cholesterol
- DOPC: dioleoyl phosphatidylcholine
- EGTA: Ethylenebis (oxyethylenenitrilo) tetraacetic acid
- DOPG: dioleoyl phosphatidylglycerol
- IgG: Immunoglobulin G
- TO: triolein
- W/O: water-in-oil emulsion
- W/O/W: water-in-oil-in-water multiple emulsion

REAGENTS

Calcein (2',7'[(bis[carboxymethyl]amino)methyl]-fluorescein); chloroauric acid (hydrogen (tetrachloroaurate) trihydrate; cholesterol; glass beads, (acid washed, Type 1-W, 75-150 microns; N-octylglucoside (N-octyl-beta-D-glucopyranoside); egg lecithin (L-alpha-phosphatidylcholine); Span 80 (sorbitan monooleate); and tannic acid were purchased from Sigma Chemical Co. (St. Louis, Mo.).

Agarose (Sea Prague low-gelling temperature agarose) was purchased from FMC Corporation (Rockland, Me.).

Bovine serum albumin (BSA) (fatty acid-poor) was from Calbiochem-Behring Corp. (La Jolla, Calif.).

Mouse IgG$_{2a}$ a monoclonal antibody against mouse major histocompatability antigen H-2K$^k$ was provided by Mrs. N. E. Norley of the University of Tennessee.

Agarose-gelatin microspherules containing colloidal gold particles were prepared using three main steps, each of which is described in detail below.

EXAMPLE 1

Preparation of Prevesicles Containing Agarose-Gelatin

Agarose-gelatin, calcein, buffer solution, N-octyl-glucoside, and glass beads were added to a test tube; the amounts and compositions are indicated in Table 1. The constituents were mixed by heating in a water bath (about 70° C.) and shaking.

In a separate test tube, cyclohexane, egg lecithin, Span 80, and ethyl alcohol were added according to the compositions shown in Table 1.

TABLE 1

| Reagents used for preparation of solid-core prevesicles | |
|---|---|
| Contents in aqueous phase | |
| 5.33% agarose and 2.67% gelatin melted in a 70° C. water bath | 200 micro-l |
| 1 M N-octylglucoside in water | 80 micro-l |
| 5 × L buffer | 80 micro-l |
| 50 mM calcein | 40 micro-l |
| Glass beads | 0.6 g |
| Contents in organic phase | |
| Egg lecithin | 53.3 micromoles |
| Cyclohexane (water-saturated) | 3880 micro-l |
| Ethanol 100% | 120 micro-l |
| Span 80 | 10 micromoles |

Both tubes were heated in a water bath (about 70° C.) for 3 min. The organic phase in one tube was transferred with a pipette to the aqueous phase in the other. The aqueous phase containing agarose-gelatin was emulsified by shaking and vortexing for 1 min. while the tube was still warm. Glass beads were included in the system to increase the mechanical agitation.

The same pipette was then used to transfer the water-in-oil emulsion (excluding the glass beads) into another tube. The temperature of the emulsion was kept at about 70° C. by inserting the tube into the water bath for a few minutes.

The emulsion was further sonicated for 30 sec. in a bath type sonicator (Laboratory Supplies, Inc.; Hicksville, N.Y.) to further reduce the size of the agarose-gelatin droplets. The tube was immediately placed in an ice-water bath for about 20 sec. to cool down the suspension, thus causing solidification of the agarose-gelatin, which has a gelling temperature of about 25° C.

At this point, spherical gel beads of different sizes were obtained.

This procedure was repeated until finally about 40 ml of prevesicles suspended in organic solvent was obtained. The crude mixture was then fractionated into three different sizes by differential centrifugation, as follows:

(a) Centrifuge the crude emulsified mixture at 500 rpm for 1 min. at room temperature; the supernatant contains fluorescent prevesicles with solid cores of agarose-gelatin of various sizes suspended in continuous organic phase; precipitate contains very large spherules or unemulsified agarose-gelatin aggregates (discarded).

(b) The supernatant from (a) is centrifuged at 2000 rpm for 10 min. at room temperature. The resulting precipitate comprises a yellow pellet of large diameter prevesicles with diameters ranging from about 0.5 to 10 microns (save).

(c) The supernatant from step (b) is a yellow turbid suspension which is further centrifuged at 3000 rpm for ten min. at 4° C. This affords a yellow precipitate which comprises prevesicles of medium size with diameters ranging from about 0.2 to 2.0 microns (save).

(d) The supernatant from step (c) is a yellow translucent suspension which is centrifuged at 8000 rpm for 20 min. at a temperature from about 4° to 10° C. The resulting precipitate comprises a thin layer of pelleted prevesicles containing agarose-gelatin with diameters ranging from about 0.1 to 0.5 microns. The final supernatant is discarded.

EXAMPLE 2

Preparation of Microspherules from Prevesicles

The emulsified agarose-gelatin prevesicles from Example 1, step (d) were extracted with organic solvents to remove lipids and then transferred to the aqueous phase, to enable them to be penetrated by reagents used for the formation of colloidal gold.

The details of this step are indicated in as follows:

The prevesicles are resuspended in hydrated cyclohexane by sonication (vol. ratio of solvent to prevesicles $\geq$ 500:1). This suspension is centrifuged at 8000 rpm for 20 min. at from 4° to 10° C. to remove lipids and surfactants. The supernatant is then discarded.

The thin layer of yellow pellet is resuspended in hydrated ether by sonication (vol. ratio of solvent to precipitate $\geq$ 500:1). This suspension is centrifuged at 8000 rpm for 20 min. at from 4° to 10° C. The supernatant is then discarded.

The thin layer of orange-yellow pellet of microspherules are resuspended in excess distilled water by sonication and this suspension is centrifuged at 8000 rpm for 20 min. to remove the ether, fluorescent dye and other water soluble components. The supernatant is discarded and the remaining colorless pellet of microspherules is used in Example 3.

EXAMPLE 3

Introducing Colloidal Gold into the Matrix of Microspherules

Colloidal gold was generated inside the microspherules with a concentration- and pH-dependent reaction between tannic acid and gold chloride.

Briefly, in 0.05 M sodium hydrogen maleate buffer, pH 6.0, 0.06% tannic acid was reacted at room temperature with an equal volume of gold chloride solution in a concentration range of 0.06–1.12%, to form rose-red colloidal gold particles with an average diameter of about 100–140 A.

The lower the concentrations of both reagents, the smaller the resulting colloidal particles were. After colloidal gold particles were introduced into the microspherules, they were coated with protein to prevent them from aggregating. Such treatment also endows the microspherules with special surface characteristics.

Both BSA-coated and IgG-coated microspherules have been prepared. The procedure for making protein-coated microspherules may be summarized as follows:

EXAMPLE 4

Preparation of Liposomes - Procedure A 50 microliters of pelleted AuSC (average diameter around 0.5 microns) were washed twice and resuspended by sonication in 100x volume of 0.02% bovine serum albumin and 0.02% NaN$_3$ and then collected by centrifugation at 8000 rpm for 15 min.

The protein treated AuSC were washed with 10 ml of water and 10 ml of 0.15 M sucrose and collected by centrifugation at 8,000 rpm for 15 min. Then, 1 ml of 0.15 M sucrose was added to make a suspension by sonication. The concentration of AuSC in sucrose solution was about 5%.

The suspension was transferred to an organic phase containing DOPC:Ch:DOPG:TO (4.5, 4.5, 1, and 1 micromoles, respectively) in 1 ml of chloroform:ether (1:1). The mixture readily formed a W/O emulsion by hand shaking. The emulsified aqueous particles in suspension were further reduced in size by strong vortexing for 10 minutes.

The W/O emulsion was then divided into two portions, and each portion (about 1 ml) was transferred to another tube containing 2.5 ml of 0.2 M sucrose. The W/O emulsion was secondarily emulsified by applying the mixture to a Vortex-Genie (Scientific Industries, Inc., Bohemia, N.Y.) at a speed setting of 6-7 for 2 × 30 sec. to make a W/O/W multiple emulsion.

The final W/O/W emulsion collected from both tubes was combined into a flask and the organic solvent was evaporated at about 35°–37° C. under a stream of nitrogen with gentle swirling. AuSCL were formed after the solvent had completely evaporated. Then 4.5 ml of 5% dextrose were added to the AuSCL suspension. The liposomes were collected by centrifugation at 600 rpm for 5 min. and the pellets were resuspended in 2 ml of 5% dextrose.

EXAMPLE 5

Preparation of Liposomes - Procedure B

Bovine serum albumin coated and pelleted AuSC (10 micro-1) were dispersed in 1 ml of chloroform containing 20 micromoles of dipalmitoyl phosphatidylcholine and 10 micromoles of cholesterol (Ch). AuSC were then collected by centrifugation at 8000 rpm for 20 min. at 4° C., and resuspended in DOPC:Ch:DOPG (9, 9, and 1 micromoles, respectively) in 3 ml of Freon 114: ether (1:1), at 4° C.

After sonication for 1 minute, the suspension was added dropwise to 0.15 M sucrose and $\frac{1}{4}$ strength L buffer, pH 7.4 (L buffer: 10 mM Hepes, pH 7.4; 1 mM EGTA and 150 mM NaCl).

This mixture was vortexed for 1 minute, and evaporated with a stream of nitrogen at 4° C. for 10 min. and then evaporated at room temperature until all organic solvent was removed. The resulting AuSCL was dialysed overnight at room temperature against 1 liter of L buffer, pH 7.4, to remove any residual organic solvent.

EXAMPLE 6

The AuSCL obtained from procedure B were fixed in 2% glutaraldehyde in 0.05 M phosphate buffer, pH 7.4, containing 0.2 M sucrose for 1 hr.; collected by centrifugation at 500 rpm for 5 min.; post fixed in 2% OsO$_4$ in 0.05 M phosphate buffer, pH 7.4, for 30 min.; washed with water overnight; pre-embedded in 3% agarose and en bloc stained in uranyl acetate overnight; dehydrated through graded series of dioxane and embedded in LX-112 resin (Ladd Research Industries, Inc. Burlington, Vt.).

EXAMPLE 7

AuSCL obtained from procedure A were treated according to the procedures of Example 6, except for being post fixed in 1% OsO$_4$ in L buffer, pH 7.4, and dehydrated with acetone. Ultrathin sections were cut with a diamond knife on a Reichert Om U3 ultramicrotomel (Vienna) and collected on Formvar-coated copper grids. Samples were examined in a Hitachi H-600 electron microscope.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of forming solid core liposomes comprising the steps of:
   (a) forming prevesicles with encapsulated solid cores consisting essentially of a polymer gel in an organic solvent containing one or more emulsifiers;
   (b) extracting lipophilic components from the prevesicles to obtain microspherules; and
   (c) encapsulating the microspherules in liposomes formed from a lipid mixture consisting essentially of phosphatidylcholine or derivatives thereof; one or more negatively charged lipids, cholesterol and triolein.

2. The method of claim 1, wherein the phosphatidylcholine derivative is dioleoyl phosphatidyl choline.

3. The method of claim 1, wherein the negatively charged lipid is a phospholipid.

4. The method of claim 3, wherein the negatively charged phospholipid is phosphatidylglycerol or a derivative thereof.

5. The method of claim 4, wherein the derivative of phosphatidylglycerol is dioleoyl phosphatidyl glycerol.

6. The method of claim 1, wherein the lipid mixture consists essentially of dioleoyl phosphatidylcholine, cholesterol, dioleoyl phosphatidylglycerol, and triolein.

7. The method of claim 1, wherein the formation of the prevesicles takes place in a mixed solvent system consisting essentially of an aqueous phase containing one or more emulsifiers and an organic phase containing one or more emulsifiers.

8. The method of claim 7, wherein the mixed solvent system consists of a mixture which includes n-octylglucoside, Hepes buffer, EGTA, NaCl, calcein and glass beads, cyclohexane, egg lecithin, Span 80, and absolute ethanol.

9. The method of claim 8, wherein the molar ratio of N-octylglucoside to egg lecithin is 1.5:1.

10. The method of claim 8, wherein the concentration of ethanol in the organic phase is about 3%.

11. The method of claim 1, wherein the liposome encapsulation of step (b) is conducted by a multiple emulsion method.

12. The method of claim 11, wherein the multiple emulsion formed in step (b) is a water/oil/water emulsion.

* * * * *

UNITED STATES PATENT AND TRADEMARK OFFICE
CERTIFICATE OF CORRECTION

PATENT NO. : 4,839,111
DATED : June 13, 1989
INVENTOR(S) : Leaf Huang

It is certified that error appears in the above-identified patent and that said Letters Patent is hereby corrected as shown below:

At page 1, before the BACKGROUND OF THE INVENTION, please insert the following:

--STATEMENT OF GOVERNMENT SUPPORT

This invention was supported in part by funding provided by the United States Government under National Cancer Institute Grant No. CA 24553. Thus, the Government of the United States has certain rights in this invention.--

Signed and Sealed this

Eighth Day of May, 1990

Attest:

HARRY F. MANBECK, JR.

Attesting Officer

Commissioner of Patents and Trademarks